United States Patent [19]

Sigl

[11] Patent Number: 5,361,410
[45] Date of Patent: Nov. 8, 1994

[54] PADDING DEVICE FOR PROTECTING THE HUMAN BODY AGAINST IMPACT

[76] Inventor: Klaus Sigl, Rosenheimerstrasse 44a, D-8018 Grafing, Germany

[21] Appl. No.: 802,381

[22] Filed: Dec. 4, 1991

[30] Foreign Application Priority Data

Dec. 10, 1990 [DE] Germany .................. 9016713[U]

[51] Int. Cl.⁵ .......................................... A41D 13/00
[52] U.S. Cl. ................................................ 2/2; 2/22; 2/23; 2/267
[58] Field of Search ................ 2/2, 2.5, 22, 23, 24, 2/267; 602/5, 11, 12, 14, 21, 22, 23, 41, 47, 60, 62, 63, 64

[56] References Cited

U.S. PATENT DOCUMENTS

| | | |
|---|---|---|
| 2,785,407 | 3/1957 | Reeder . |
| 3,044,075 | 7/1962 | Rawlings ................... 2/22 |
| 3,176,686 | 4/1965 | Barnes . |
| 3,500,472 | 3/1970 | Castellani ................... 2/2 |
| 4,136,226 | 1/1979 | Gilman . |
| 4,373,211 | 2/1983 | Goudreau et al. . |
| 4,425,667 | 1/1984 | Harrison ................... 2/2 |
| 4,765,319 | 8/1988 | Finnieston et al. ........... 602/21 |
| 4,872,215 | 10/1989 | Sliger ................... 2/2 |
| 5,105,473 | 4/1992 | Valtakari ................... 2/2 |

FOREIGN PATENT DOCUMENTS

| | | |
|---|---|---|
| 0108865 | 7/1983 | European Pat. Off. . |
| 0246462 | 4/1987 | European Pat. Off. . |
| 2259552 | 2/1974 | France . |
| 2472399 | 7/1981 | France ................... 2/22 |
| 3901191 | 8/1989 | Germany . |
| 9001883 | 8/1990 | WIPO . |
| 9205717 | 4/1992 | WIPO . |

Primary Examiner—Clifford D. Crowder
Assistant Examiner—Gloria Hale
Attorney, Agent, or Firm—Dena Meyer Weker

[57] ABSTRACT

A device for protecting the human body against impacts and blows is provided that may be used integral with a garment or separately. The device consists of a hard core material and a padding part which further comprises a foam material with closed parts wherein the hard core material and padding part have perforations in a predesigned configuration. The padding part may also be equipped with a functional lining that is water vapor permeable, windproof and waterproof. These devices are particularly useful as a protective insert in sports uniforms and protective helmets and may also be used as a splinting device such as a cast.

9 Claims, 3 Drawing Sheets

PADDING DEVICE FOR PROTECTING THE HUMAN BODY AGAINST IMPACT

FIELD OF THE INVENTION

The invention relates to a padding device for protecting certain parts of the human body against impacts, blows or the like. Such protection devices for the human body may be used in state of the art sports uniforms or garments such as ice hockey pants where they serve as protectors for the kidneys, buttocks or thighs. For this purpose, they are sewn into the sports pants at the appropriate places or they are sewn into special pockets of the uniform. Alternatively they may be worn separate from the sports garment.

BACKGROUND OF THE INVENTION

There are different constructions for body protection devices that are useful in sports activities where there is potential for bodily injury. A common element of conventional equipment is a core of hard material corresponding approximately to the shape of the area to be protected. The hard material core may consist of plastic, metal or a rigid, hardened plastic foam. Another common feature of this equipment is the padding that is provided on both sides of the hard material core. In state of the art equipment this padding part consists of a foam with closed pores or with open pores. Another type of equipment incorporates a film with bubble-shaped air pockets as is commonly used in pressure-resistant packing foil. These pockets are typically installed in the equipment so as to face the body. These air pockets may be used instead of or in addition to the foam padding.

The inner side of such a body protection device is usually supplied with a lining. The outer side consists of the outer material of the sports garment such as a polyamide fabric or a textile material coated with polyester.

The hard material cores are intended to fend off impacts, shocks, punches and the like. The inner padding parts serve to absorb the force exerted by an impact, protect the wearer's body and at the same time increase the wear comfort of the uniform incorporating such protectors. The padding at the outer side of the hard material absorbs blows dealt to the above-mentioned body protectors and protects athletes colliding with other athletes from being hurt by bumping against the hard core of the body protection device.

When playing rigorous sports such as ice hockey, the players sweat heavily as they get very hot. A large surface of the uniform is provided with body protectors in order to protect the players against impacts and blows as well as possible. Since the hard material cores of the body protectors are impermeable to water and water vapor, perspiration moisture collects under the protectors, entailing an unpleasant amount of trapped heat.

When an open-pored foam is used at the inside of the hard material core, this foam absorbs the sweat emitted by the athlete's body. As the perspiration moisture emitted by one player during an activity may amount to several liters of water, the amount of perspiration trapped within the open-pored foam may be enormous. This not only detracts from the wear comfort of the sports uniform but also increases their weight.

When the padded parts of the protectors consist of a foam with closed pores, they will not be soaked in sweat. In this case, however, the whole sweat quantity collects on the surface of the player's body or runs down his body inside of the body protectors of the uniform.

Conventional protective gear for use in sports activities are thus very unpleasant to wear.

There is a need to provide body padding protectors of considerably increased wear comfort.

SUMMARY OF THE INVENTION

A body protection device is provided with a hard material core and a padding which consists of a foam with closed pores and which covers the core at the side facing the human body. Both the hard material shell and the padding part are perforated in the direction perpendicular to their longitudinal extension. Preferably the perforations of the hard material core and the padding are aligned relative to each other, at least in situations when the hard material and the padding are firmly linked with each other.

When both sides of the hard material core are covered by a padding, both padding parts are provided with cross perforations. These cross perforations provided by the invention make the body protectors water vapor permeable, so that water vapor produced by perspiration can escape through the protectors and an accumulation of sweat on the wearer's body can be avoided or at least greatly reduced. Since a foam with closed pores is used for the padding, the foam does not become soaked in perspiration liquid.

Sweat which condenses on the body or within the protector runs off through the holes in the protector.

When the protector described in the present invention is integrated into a garment, such as ice hockey pants, the material at the outside of the body protection device should preferably be waterproof and water vapor permeable, for instance a laminate with a textile fabric on its outside and a functional layer which is waterproof and water vapor permeable on its inside. If the garment is worn in rain or, as it is the case for ice hockey pants, is in contact with molten ice, water from outside is kept off the wearer's body, whereas water vapor produced when the wearer sweats can escape through the cross perforations of the protector and the water vapor permeable outer material.

The range of applications of the protection devices provided by the present invention is enormous. They may be used as inserts or paddings in garments, particularly in sports garments, such as pants and jerseys for ice hockey, football, soccer, rugby, and handball. Furthermore, they may also be used independently of garments. One example are leg protectors which are loosely inserted between the shinbone and stockings by soccer players before a match.

There are numerous other applications for protectors of the type described herein. Helmets, for instance, may either incorporate such protectors or may fully consist of such protectors.

Another example are safety workwear shoes, which are provided with a rigid protection cap, at least in the toe area.

Other applications of the body protection devices include body splinting devices to be used instead of plaster casts for the treatment of bone fractures, such as broken arms or legs.

In most applications of this novel body protection device, it is advantageous to use a water vapor permeable material on the outside of the body protection device, which is also windproof and/or waterproof. Further, the device not only applies to garments, protective helmets and safety shoes, but also to devices which serve to immobilize broken limbs. In all of these cases, the outer material must be permeable to water vapor in order to maintain the function of the cross perforations of the body protection device. On the other hand, the cross perforations allow water to easily penetrate the body protection device, which may be prevented by a waterproof outer material. For this purpose, the outer material is provided with a state of the art waterproof, water vapor permeable functional layer, preferably in the form of a laminate with a water permeable outer material and the functional layer.

The microporous polymer material can be made from any polymer material by means of any state of the art process, provided it is suitable to produce a functional film layer and meets the desired characteristics. The polymers suitable for forming a microporous polymer matrix include polyolefins, such as polyethylene-polypropylene-copolymers, polyethylene-terephthalates, polycaprolactam, polyvinylidenefluoride, polybutylene-terephthalate, polyester copolymers and polytetrafluoroethylene. The preferable microporous layer is expanded porous polytetrafluoroethylene.

DETAILED DESCRIPTION OF THE INVENTION

The invention is best understood with reference to the accompanying figures.

Figure 1:
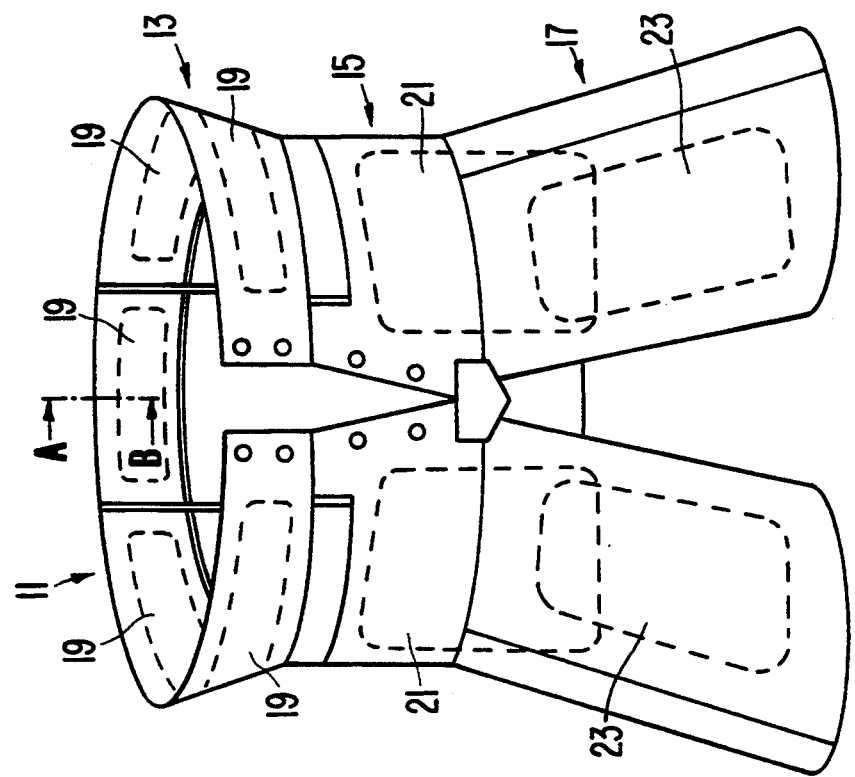
FIG. 1 is a schematic drawing of ice hockey pants with several body protection devices.

FIG. 1 is a schematic view of the ice hockey pants 11 with a waist area 13, a hip area 15 and a thigh area 17. The waist area 13 incorporates waist and kidney protectors 19. The hip area 15 incorporates hip protectors 21. The thigh area 17 incorporates thigh protectors 23.

Figure 2:
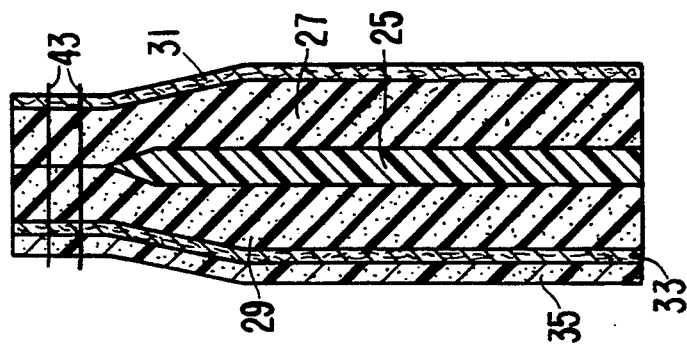
FIG. 2 is a partial cross section of ice hockey pants with a conventional body protection device.

FIG. 2 is a cross-sectional view of a state of the art body protection device for ice hockey pants 11. The core of the protection device is a hard material core 25 in the shape of a plate, sometimes available with a curvature to follow the body's contours. The hard material core 25 consists of a hard plastic material. The hard material core 25 serves as a protection against impacts and blows.

Each side of the hard material core 25 is provided with a padding, namely an inner padding part 27 facing the body and an outer padding part 29 at the other side. Both padding parts 27 and 29 consist of a foam with closed pores.

The inner side of the inner padding part 27 is provided with an inner lining 31. The outer side of the outer padding part 29 is provided with an outer lining 33. An outer material 35 consisting of a polyamide fabric is arranged above the outer lining 33.

FIG. 2 shows a cross section of a waist and kidney protection 19 along a cut line A–B of FIG. 1. This figure at the same time shows the constructions of other body protection devices, namely the hip protector 21 and the thigh protector 23.

Figure 3:
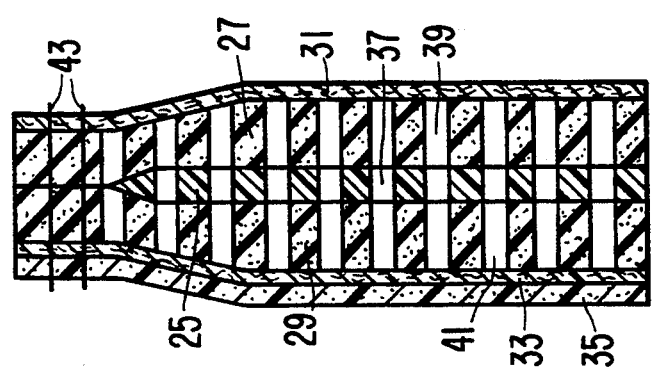
FIG. 3 is a cross section of ice hockey pants with a body protection device as provided by the present invention.

FIG. 3 also shows a cross section, along line A–B of FIG. 1, of a waist and kidney protector 19 similar to that shown in FIG. 2. Similar to conventional protective gear, the present invention incorporates a hard material core 25, an inner padding part 27 and an outer padding part 29. According to the invention, the hard material core 25 and the two padding parts 27 and 29 are, however, provided with perforations 37, 39 and 41 in the direction perpendicular to their longitudinal extension. Preferably, the hole diameter is relatively large to assure a good water vapor permeability. The hole diameter may be, for instance, 4 mm.

In the body protection device provided by the invention, the inner side of the inner padding part 27 is covered by an inner lining 31, whereas an outer lining 33 is arranged at the outside of the outer padding part 29. An outer material 35 of the body protection device preferably consists of a laminate with a textile fabric as the outer material and a waterproof, water vapor permeable and windproof functional layer at the inside of material 35. A preferable waterproof water vapor permeable functional layer is expanded porous polytetrafluoroethylene made in accordance with the teachings of U.S. Pat. Nos. 3,953,566 and 4,187,390. Alternatively another preferred material includes a material comprising a composite material of a hydrophobic material such as expanded PTFE and a hydrophilic material made in accordance with the teachings of U.S. Pat. No. 4,194,041.

Since the outer material 35 is waterproof, water cannot penetrate the body protection device from outside so that the wearer of the ice hockey pants 11 is kept dry. The outer material is, however, permeable to water vapor which is transported through the inner lining 31, the perforations 37, 39 and 41 and the outer lining 33.

The hard material core 25, the padding parts 27, 29, the inner lining 31, the outer lining 33 and the outer material 35 are preferably only loosely aligned and attached to each other by two parallel seams 43 in the area shown as their top in FIG. 3. Alternatively, at least the hard material core 25 and the two padding parts 27 and 29 may be adhesively bonded to each other. Particularly in the latter case, it is advisable to congruently align the perforations 27, 39 and 41 in order to assure a good water vapor permeability. The hard material core 25 and the two padding parts 27 and 29 are preferably laid one above the other before the perforations are made to optimally align the holes 37, 39, 41. If the hard material core 25 and the two padding parts 27 and 29 are not adhesively bonded but only loosely laid next to each other, the perforations 37, 39 and 41 need not necessarily coincide with each other because wearing the ice hockey pants 11 will cause relative movement in the cross direction between the hard material core 21 and the two padded parts 27 and 29, which will cause the formation of air gaps in between these three parts also connecting non-aligned perforations 37, 39 and 41 with each other.

The body protection device shown in FIG. 3 can be attached to the ice hockey pants 11 by the seams 43. Alternatively, the body protection devices may be accommodated in pockets of the sports uniform arranged between the outer material 35 and outer lining 33 and the inner lining 31. The body protection devices may also be supported as a separate device.

Figure 4:
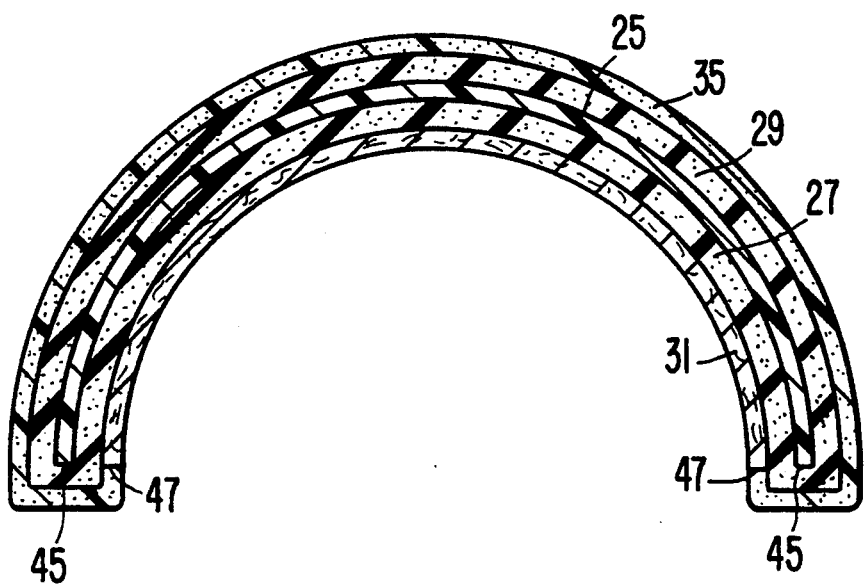
FIG. 4 is a schematic cross section of a protective helmet designed as described in the present invention.
Figure 5:
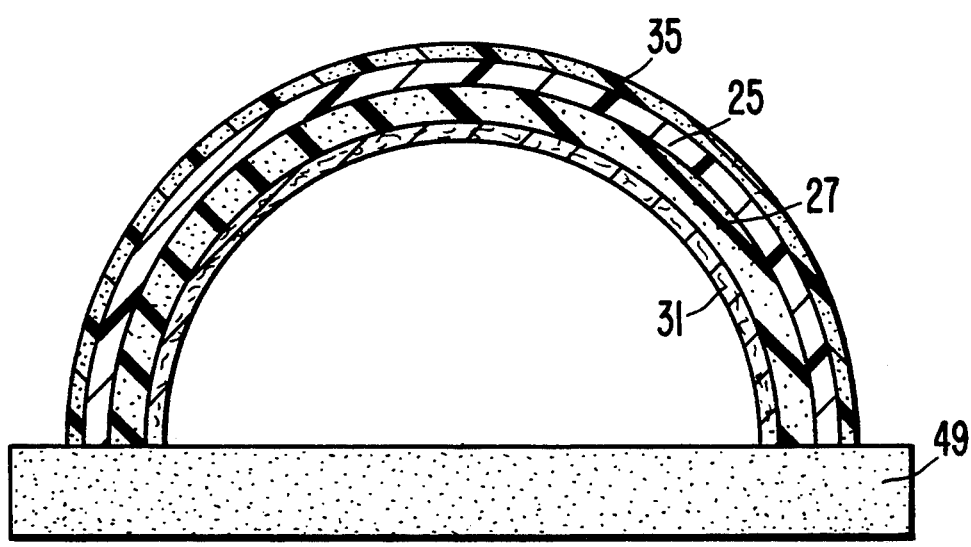
FIG. 5 is a schematic cross section of a safety shoe as provided by the present invention.
Figure 6:
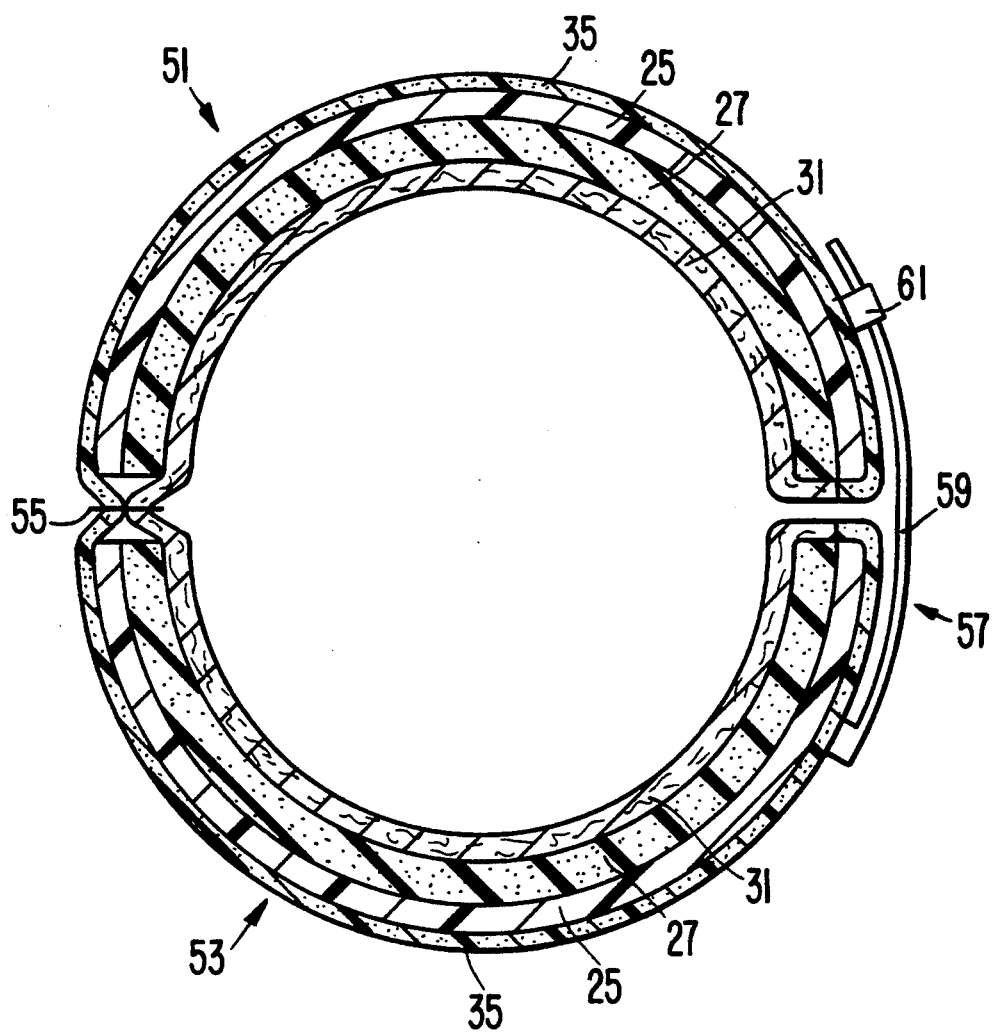
FIG. 6 is a schematic cross section of a body splinting device as provided by the present invention.

Other applications, in addition to use as a protective device for hockey players are also within the scope of this invention, as shown in FIGS. 4 to 6. For the sake of simplicity, the same reference numbers will be used wherever layers and materials are the same as those shown in FIG. 3. What is not shown in FIGS. 4 to 6 are the cross perforations in the hard material shells and paddings. The invention, however, provides for these perforations in these cases corresponding to perforations 37, 39 and 41 as shown in FIG. 3.

FIG. 4 is a schematic cross section of a protective helmet. The helmet is formed by a single body protection device constructed in the shape of a helmet. The core and the protection against impacts and blows is afforded by the hard material core 25 which is embedded into a padding part constituting both the inner padding part 27 and the outer padding part 29 and which is guided around the edge 45 of the hard material core 25. The inner side of the inner padding part 27 is covered by the inner lining 31. The outer side of the outer padding part 29 is covered by the outer material 35 which is guided around the edge 45 of the hard material core 25. By means of a seam 47 it is sewn to the lining 31 in such a way that the seam runs in the inner edge area of the inner padding part 27.

Since both the hard material core 25 and the two padding parts 27 and 29 are provided with the cross perforations not drawn in FIG. 4, the protective helmet is water permeable. The outer material is preferably equipped with a waterproof, water vapor permeable functional layer in order to make the helmet impermeable to water and at the same time allow water vapor to escape through the perforations. Similar to that described above, the waterproof water vapor permeable functional layer is preferably made of expanded porous PTFE.

It is not necessary to completely embed the hard material core 25 in a padding material. The outer padding part 29 may also be dispensed with and the outer material 35 may be directly mounted to the hard material core 25.

In many cases it may be desirable to use a hard material, such as plastic, for the protective helmet. In these cases, the hard material core 25 may serve as the outer material and a waterproof, windproof and water vapor permeable functional layer may be arranged within the hard material core 25 instead of the construction shown in FIG. 4.

FIG. 5 shows the schematic design of a front cross section of safety shoe incorporating a protection device against impacts and blows in the form of a hard material core 25, at least in the toe area of the shoe. In the embodiment shown in FIG. 5 an inner padding part 27 is arranged at the inner side of the hard material core 25. Additionally, an outer padding part 29 may be arranged at the outside of the hard material core 25. The hard material core 25 and the inner padding part 27 as well as in some cases an outer padding part are perforated in the cross direction, although this is not shown in FIG. 6. The inner side of the inner padding part 27 is covered with a lining 31 and the outer side of the hard material core 25 is covered with an outer material 35. The outer material 35 is the material of the safety shoe upper. If the shoe must be waterproof, the outer material 35 can be provided with a waterproof, water vapor permeable functional layer to extend the water vapor permeability afforded by the perforations of the hard material core 25 and the inner padding part 27 to the outer material.

The functional layer may also be located within the hard material core 25 to afford a better mechanical protection.

An outside 49 is injection-molded to the lower edge of the outer material 35, the hard material core 25, the padding part 27 and the inner lining 31. Any other outsole may also be used.

FIG. 6 is a schematic cross section of a tubular splinting device for treating broken limbs of the human body, such as a broken arm or leg. In the embodiment shown in FIG. 6, the body splinting device consists of two half-shells, namely one upper half-shell 51 and one lower half-shell 53. Each half-shell 51 and 53 is provided with a basically semicircular hard material core 25 and with an inner padding part 27 at its inside, both provided with cross-perforations (not shown in FIG. 6).

The inner side of each inner padding 27 is covered with an inner lining 31 to enhance the wear comfort of the body splinting device. Each hard material core 25 may be covered with an outer material 35 which may incorporate a waterproof, water vapor permeable functional layer in order to prevent water from penetrating through the perforations of the hard material cores 25 and the inner padding part 27. The functional layer may also be arranged within the hard material cores 25. The functional layer protects the wearer of the splinting device outdoors, in rain or snow. Such a body splinting device does not have to be taken off when the patient takes a shower. This is an improvement of the state of the art plaster splinting devices, which need to be covered with a plastic film or bag before contacting them with water.

Since both hard material cores 25 usually consist of a rigid plastic material, the body splinting device shown in FIG. 6 can be folded back. For this purpose, the inner lining 31 and the outer material 35 extend over both hard material cores 25 and are attached to each other by a seam 55 running between the edges of the two hard material shells at the left side in FIG. 6. At the right edges (FIG. 6) of the splinting half-shells 51 and 53, the inner lining 31 and the outer material 35 are connected to each other (FIG. 6) without reaching up to the inner lining 31 and the outer material 35 of the opposite half-shell 53, 51. In this way, the two splinting half-shells 51 and 53 can be displaced relative to each other and thus brought into an open or closed position in such a way that the parts of the inner lining 31 and the outer material 35 which are linked by the seam 55 form a swivelling hinge.

The two unconnected edges of the two splinting half-shells 51 and 53 can be held together by means of a closing device 57 with a closing shackle 59 which is anchored in the lower half-shell 53 and guided through a closure eyelet 61 in the upper half-shell 51, in which it can engage in any desired position.

For putting on the body splinting device, the two half-shells 51 and 53 are swivelled into the open position by opening the locking mechanism between the shackle 59 and the closing eyelet 61. After the limb which is to be immobilized, a broken arm is laid into one splinting half-shell, the two half-shells 51 and 53 are brought into their closing position where they are held by means of the closure device 57. If the closing shackle 59 is of sufficient length, the body splinting device can be adapted to arms and legs of different thicknesses in that the two splinting half-shells 51 and 53 are brought into the closing position at a smaller or larger distance to each other.

If it is necessary for the device to be absolutely waterproof, the gap remaining at the closing side between the two half-shells 51 and 53 can be covered by a waterproof material. One possibility is to pull a tube consisting of an elastic laminate, which incorporates a waterproof and water vapor permeable functional layer, over the splinting half-shells 51 and 53 covering the limb which is to be immobilized. Said tube may additionally serve as a substitute for the closing device 57 and/or the outer material 35.

I claim:

1. A protective device for use on the human body with a garment comprising a hard material core having at least two sides, one side of which faces the human body, and two padding parts, each of which consists of a foam material with closed pores and in which each of the padding parts is surrounded by a nonperforated lining wherein a padding part is arranged on each side of the hard material core so that one padding is identified as the outer padding and the other padding is identified as the inner padding which is adjacent the human body, and wherein both the hard material core and padding parts have a longitudinal extension, characterized in that both the hard material core and the padding parts excluding the linings have perforations in the direction perpendicular to their longitudinal extension and wherein the outer padding part is provided with a water vapor permeable nonperforated lining at the side facing the human body.

2. A body protection device of claim 1, wherein one cross-perforated padding part consisting of a foam material with closed pores, is arranged on each side of the hard material core.

3. A body protection device of claim 1, wherein the perforations of the hard material core and the padding part are aligned.

4. The use of the body protection device of claim 1 as a protective insert in a sports garment, selected from the group consisting of hockey, ice hockey, football, rugby and handball garments.

5. A garment with at least one body protection device integrated therein said protection device comprising a hard material core and padding parts, each consisting of a foam material with closed pores and in which each of the padding parts is surrounded by a nonperforated lining, and in which each padding part is arranged on a side of the hard material core, wherein the padding parts and hard material core each have a longitudinal extension and wherein both the hard material core and the padding parts excluding the linings are provided with perforations in the direction perpendicular to their longitudinal extension and wherein the body protection device is arranged between an outer material equipped with a water vapor permeable, windproof, waterproof, and nonperforated functional layer and an inner nonperforated lining of the garment.

6. A garment of claim 5, having an inside wherein the body protection device is arranged at the inside of the garment material.

7. A garment of claim 5, wherein the outer material is equipped with a laminate incorporating the functional layer.

8. A garment of claim 5, wherein the functional layer incorporates a membrane of expanded microporous polytetrafluoroethylene.

9. A garment of claim 5, wherein at least one body protection device is designed to protect a body part from the group consisting of kidneys, buttocks, hips and thighs.

* * * * *